United States Patent
Yuzefovich et al.

(10) Patent No.: US 7,197,171 B2
(45) Date of Patent: Mar. 27, 2007

(54) NUCLEAR IMAGING

(75) Inventors: Isabella Yuzefovich, Haifa (IL); Michael Wilk, Haifa (IL)

(73) Assignee: Elgems Ltd., Tirat HaCarmel (IL)

( * ) Notice: Subject to any disclaimer, the term of this patent is extended or adjusted under 35 U.S.C. 154(b) by 716 days.

(21) Appl. No.: 10/369,146

(22) Filed: Feb. 19, 2003

(65) Prior Publication Data

US 2004/0161140 A1    Aug. 19, 2004

(51) Int. Cl.
    *G06K 9/00*    (2006.01)

(52) U.S. Cl. ............... 382/131; 600/407; 600/436; 378/120

(58) Field of Classification Search ........ 382/128–134; 378/4, 21–27, 46, 90, 92, 98.4, 98.6, 98.9, 378/101, 901, 120; 600/407, 425, 436, 321; 250/363.04, 370.09, 586; 128/915
See application file for complete search history.

(56) References Cited

U.S. PATENT DOCUMENTS

| | | | |
|---|---|---|---|
| 5,493,595 A * | 2/1996 | Schoolman ................. 378/41 |
| 5,739,539 A * | 4/1998 | Wang et al. ........... 250/363.04 |
| 5,813,985 A * | 9/1998 | Carroll ........................ 600/436 |
| 5,930,384 A * | 7/1999 | Guillemaud et al. ........ 382/154 |
| 6,002,739 A * | 12/1999 | Heumann ...................... 378/8 |
| 6,320,928 B1 * | 11/2001 | Vaillant et al. ................ 378/4 |
| 6,697,660 B1 * | 2/2004 | Robinson .................... 600/409 |

FOREIGN PATENT DOCUMENTS

WO    WO 00/75691    12/2000

* cited by examiner

*Primary Examiner*—Jingge Wu
*Assistant Examiner*—Abolfazl Tabatabai

(57) ABSTRACT

A method for producing a nuclear medicine image utilizing emission data in an iterative reconstruction process. The starting point for the iterative process is based on internal structure information. The internal structure information can be based on data that is different from the nuclear emission data used in the reconstruction itself, for example CT X-Ray attenuation data, Magnetic Resonance Imaging, Ultrasound Imaging or nuclear transmission data.

23 Claims, 1 Drawing Sheet

NUCLEAR IMAGING

FIELD OF THE INVENTION

The present invention relates to nuclear medical image generation.

BACKGROUND OF INVENTION

In nuclear medical imaging, a patient is injected with radiopharmaceutical material that dilutes and/or concentrates in the various body tissues. Gamma radiation emissions are collected from the patient utilizing gamma ray detectors, for example, gamma camera heads. These collected emissions are used to reconstruct a three dimensional image of the distribution of gamma ray sources within the patient.

Most reconstruction methods utilize filtered back projection. However, in some instances, for example, where the data is incomplete, iterative methods are used.

In some such iterative systems, a reconstruction cylinder containing the patient is defined. The intensity values are initially set to some single value over the entire cylinder and the iterative process then proceeds to correct the values based on the projection values acquired in the data collection process. Many variations of such processes are known.

The general idea of using body outline information in performing iterative reconstruction in nuclear medical imaging is known. U.S. Pat. No. 5,739,539, the disclosure of which is incorporated herein by reference, describes a method in which only regions within the body contour take part in the iterative reconstruction process. Namely, regions inside the body are set to a single non-zero value and regions outside the body are set to an initial zero value. At each iteration step, any non-zero pixels outside the body contour are also set to zero, before performing the next iteration.

In some systems, an attenuation map of the patient is obtained, to correct the image for attenuation of the gamma rays before they reach the detectors. This data may be used to determine the body contour in the prior art. Systems that determine body attenuation are described, for example, in PCT application no. PCT/IL99/00300; "Gamma Camera and CT System", published as WO 00/75691, the disclosure of which is incorporated herein by reference.

SUMMARY OF THE INVENTION

An aspect of some embodiments of the invention relates to assigning more than two different values for different areas within a reconstructed volume as a starting point for iterative reconstruction of emission data from a subject.

In an exemplary embodiment of the present invention, initial values for reconstruction are different for two or more different regions within the body volume and a third region outside the body volume.

In an exemplary embodiment of the present invention, different values for reconstruction are based upon anatomic region, tissue type, and/or attenuation within the body. The location of the different body regions may be determined by structural measurements of the subject. Such values, for example, can be generated from CT gamma or X-ray transmission measurements, Magnetic Resonance Imaging (MR) or ultrasound measurements of the subject or using a model of the patient, which may be based on the height and weight of the patient. Since attenuation measurements are generally also desired, data from CT gamma or X-ray transmission measurements are used for both attenuation correction and for carrying out the present invention.

There is thus provided, in accordance with an embodiment of the invention, a method for producing a nuclear medicine image of body tissue utilizing emission data comprising:

providing information relating to the internal structure of a patient;

providing nuclear emission data acquired from the patient;

determining initial values for an iterative three dimensional reconstruction process for the emission data, based on the internal structure information; and reconstructing an image from the emission data starting from the initial values, utilizing an iterative reconstruction process, wherein the initial values comprises more than two values.

Optionally, the initial values comprise at least two values within the volume associated with the interior of the patient.

Optionally, the initial values comprise a continuum of values within the volume associated with the interior of the patient.

Optionally, the method includes repeating the iteration process until an intermediate image of a distribution of radiopharmaceutical in the patient is superimposed on the internal structure and displaying the intermediate image.

Optionally the initial values comprise a single value for the reconstruction volume outside the body.

In an embodiment of the invention, the information related to internal construction is derived from CT X-ray attenuation data of body tissue. Alternatively or additionally, the information related to internal construction is derived from Magnetic Resonance Imaging data and/or Ultrasound imaging of body tissue and/or nuclear transmission data and or identification of different tissue regions within body tissue. Optionally, the initial values are based directly on image intensity values. Optionally, the initial values are based on different tissue densities within body tissue.

Alternatively or additionally, the initial values are based on one or more of chemical content within body tissue and tissue functionality.

There is further provided, in accordance with an embodiment of the invention, a method for producing a nuclear medicine image of body tissue utilizing emission data comprising:

providing information relating to the internal structure of a patient;

providing nuclear emission data acquired from the patient;

determining initial values for an iterative three dimensional reconstruction process for the emission data, based on the internal structure information;

repeating an iterative reconstruction process for reconstructing an image from the emission data starting from the initial values, until an intermediate image of a distribution of radiopharmaceutical superimposed on an image of structure is produced; and displaying the intermediate image.

Optionally, the initial values comprise a continuum of values within the volume associated with the interior of the patient.

In various embodiments of the invention, the information related to internal construction is derived from one or more of CT X-ray attenuation data of body tissue, Magnetic Resonance Imaging data of body tissue, Ultrasound imaging of body tissue and nuclear transmission data. Optionally, the initial values are based directly on image intensity values. Optionally, the initial values are based on different tissue densities within body tissue.

BRIEF DESCRIPTION OF THE DRAWING

Non-limiting embodiments of the invention will be described with reference to the following description of exemplary embodiments, in conjunction with the FIGURE.

DETAILED DESCRIPTION OF EMBODIMENTS

Figure 1:
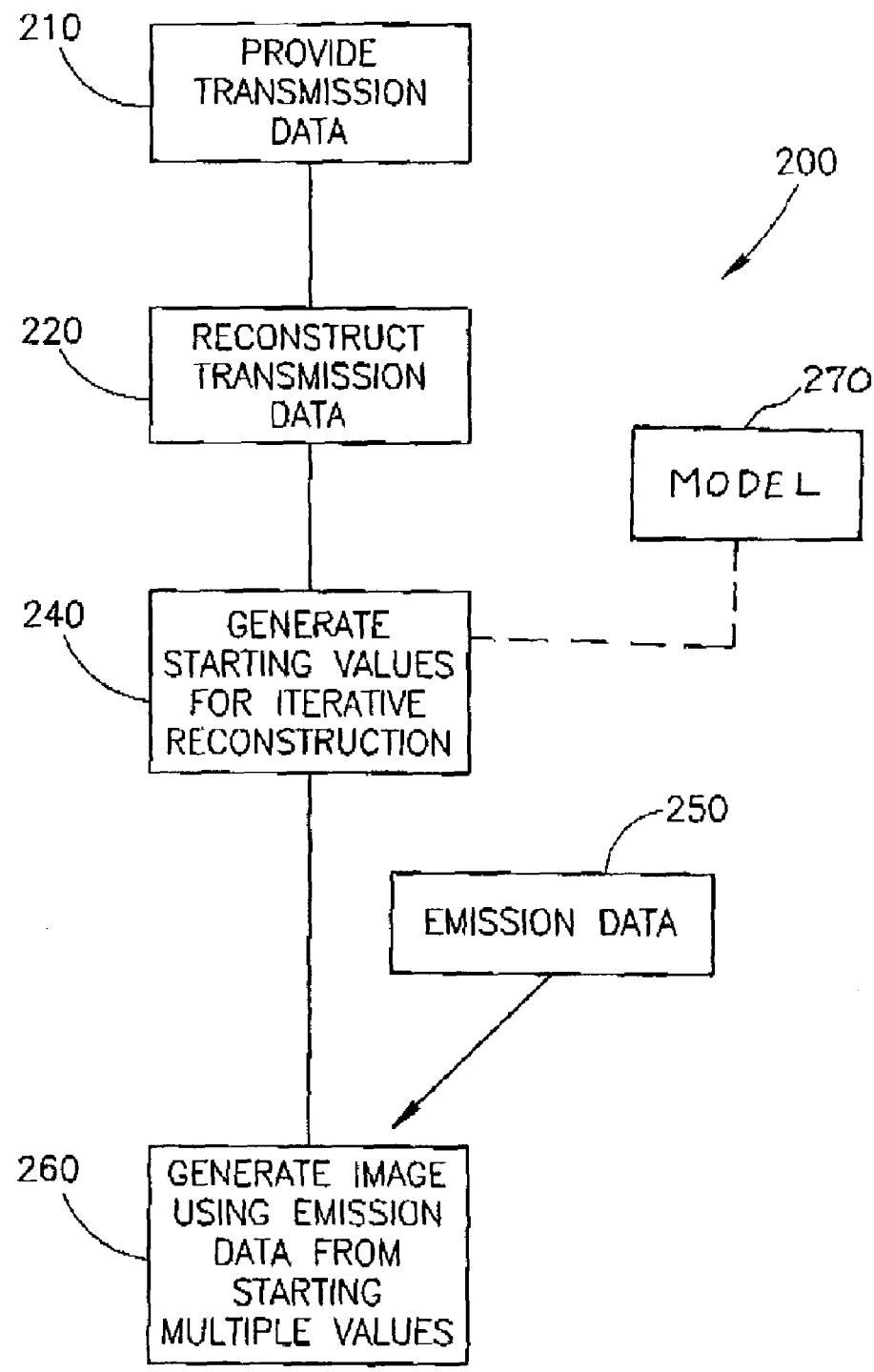
FIG. 1 is a flow chart of a process for generating sag values in nuclear medical imaging emission data.

FIG. 1 schematically shows a system 200 for generating starting values (i.e. initial values) in nuclear medical imaging emission data. At 210, transmission or other data that identifies or segments the body structure is provided. Such data could be from a CT X-ray image of the scanned volume. Alternatively, such data could be from a gamma ray CT transmission image of the scanned volume. Alternatively or additionally it could be data from MRI data. Alternatively or additionally it could be from any data suitable for construction of a structural image. By way of example, ultrasound attenuation data suitable for use with emission data could be used in step 210. Alternatively or additionally a structural model of a patient (which may be based on height and/or weight of the patient) is used (270) as part of the model for starting values.

The provided transmission data is reconstructed at 220 to generate an image of the scanned volume suitable for utilizing as starting values for emission data. By way of example, when an X-ray is used to provide transmission data, X-ray beams pass through the lungs and attenuate to give a first level of signal. Other X-ray beams travel through the body tissue surrounding the lungs to provide a second attenuation signal.

These attenuation levels are optionally reconstructed at 240 to develop a body map defining different tissue regions and a non-attenuation region for non-body volume. In the example given, the area within the body map illustrates an image slice with various attenuation areas associated with various tissues, such as lung having one attenuation range, tissue surrounding the lungs having a second attenuation range and non-body volume representing a third (non-attenuation) region. Additional segmentation may be used, which differentiates bone from other tissue.

Alternatively or additionally, nuclear magnetic resonance data is used to develop a body map defining different tissue regions and non-body volume as starting values for reconstruction utilizing emission data.

Alternatively or additionally, the area within the body map illustrates an image slice with various attenuation areas defining various different tissue types based upon chemical or structural (functional) content. As an example, such content could be based upon the amount of blood within various body tissues. As another example, chemical content could be based upon the amount of antigenic material within various body tissues. Such a means of distinguishing body tissue is highly relevant tumor detection where antigenic markers are introduced to identify and attract immune response against the tissue.

The body map, with its various tissues or regional attenuation is assigned initial values for the iteration process. By way of example, the lungs receive a value of 1, the vertebrae receive a value of 1.5, the ribs a value of 2 and a suspected tumor area receives a value of 3. Anything outside the body receives (and is set to) a value of 0. These values are only representative and may be varied depending on the expected distribution of radiation within the body. Such expectation may be based on the type of radiation source used or on the clinical situation of the particular patient.

Alternatively to defining body structures from the transmission data and using these structures to define the initial values for the iteration process, the initial values may be defined directly from the density or intensity values generated by the transmission or other structural imaging process used. Thus, for example, the starting values may be made proportional to the CT (Houndsfield) numbers.

At 250, emission data suitable for generating a three dimensional image using iteration is collected from the gamma radiation detectors for the entire scanned cylindrical volume. At 260, the body and non-body starting values generated at 240 are used for starting values of iterative reconstruction of the emission data at 250. Any method for iterative reconstruction known in the art may be used, since the present invention is concerned with setting the initial values for reconstruction and not with the actual reconstruction algorithm itself In some embodiments of the invention, the image values for pixels outside the body is kept at zero for all iterations.

Assigning different starting values to different portions of the body serves to provide starting values that are closer to final results. The number of steps required to reconstruct the data is lessened and/or the resultant image contains less noise and fewer artifacts. Since in an iterative approach a starting point with high accuracy is not necessary, neither with respect to extents, position or starting values, the exact values to be assigned are not critical. However, the speed of convergence is improved, if the initial distribution of values is determined with the expected final distribution taken into account.

When CT values are used as the starting point for the iterative reconstruction algorithm, as the iterations progress, the image will transform from a structural image (the NM or X-Ray CT image) to a functional image (the final NM image), showing only the distribution of radiopharmaceutical. Intermediate images (i.e., between the initial and final images) will show structure (with decreasing contrast, as the iteration progresses), with the radiopharmaceutical distribution superimposed thereon. The intensity and contrast of the radiopharmaceutical part of the image increases with the number of iterations. Thus, some of the intermediate images will show both structure and function, without the need for combining two images.

The present invention has been described using non-limiting detailed descriptions of embodiments thereof that are provided by way of example and are not intended to limit the scope of the invention Variations of embodiments described will occur to persons of the art. In addition, while preferred embodiments of the invention have been described as having certain groups of features, some preferred embodiments of the invention may include fewer of more of the features or other combinations of features. Furthermore, the terms "comprise," "include," and "have" or their conjugates shall mean: "including but not necessarily limited to." The scope of the invention is limited only by the following claims:

The invention claimed is:

1. A method for producing a nuclear medicine image of body tissue utilizing emission data comprising:

providing information relating to the internal structure of a patient;

providing nuclear emission data acquired from the patient;

determining initial values for an iterative three dimensional reconstruction process of the emission data, based on the internal structure information; and reconstructing an image from the emission data starting from the initial values, utilizing an iterative reconstruction process, wherein the initial values comprises more than two values; and wherein the information relating to the internal structure is derived from at least one member of a group consisting of data from CT X-ray attenuation, Magnetic Resonance Imaging, Ultrasound imaging and nuclear transmission.

2. A method according to claim 1, wherein the initial values comprise at least two values within a volume associated with the interior of the patient.

3. A method according to claim 1, wherein the initial values comprise a continuum of values within the volume associated with the interior of the patient.

4. A method according to claim 3, wherein the iteration process is repeated until an intermediate image of a distribution of a radiopharmaceutical in the patient is determined and superimposing the intermediate image on the internal structure and displaying the superimposed image.

5. A method according to claim 1 wherein the initial values comprise a single value for a reconstructed volume outside the body.

6. A method according to claim 1 wherein the information relating to the internal structure is derived from CT X-ray attenuation data.

7. A method according to claim 6 wherein the initial values are based directly on image intensity values.

8. A method according to claim 1 wherein the information relating to the internal structure is derived from Magnetic Resonance Imaging data.

9. A method according to claim 1 wherein the information relating to the internal structure is derived from Ultrasound imaging.

10. A method according to claim 1 wherein the information relating to the internal structure is derived from nuclear transmission data.

11. A method according to claim 1 wherein the initial values are based on identification of different tissue regions within body tissue.

12. A method according to claim 11, wherein the initial values are based on different tissue densities within body tissue.

13. A method according to claim 1, wherein the initial values are based on chemical content within body tissue.

14. A method according to claim 1, wherein the initial values are based on tissue functionality.

15. A method for producing a nuclear medicine image of body tissue utilizing emission data comprising:

providing information relating to the internal structure of a patient;

providing nuclear emission data acquired from the patient;

determining initial values for an iterative three dimensional reconstruction process for the emission data, based on the internal structure information, the internal structure information being other than the emission data used to reconstruct the nuclear image;

repeating an iterative reconstruction process for reconstructing an image from the emission data starting from the initial values, until an intermediate image of a distribution of radiopharmaceutical superimposed on an image of structure is produced; and displaying the intermediate image.

16. A method according to claim 15 wherein the initial values comprise a continuum of values within a volume associated with the interior of the patient.

17. A method according to claim 15 wherein the information relating to the internal structure is derived from CT X-ray attenuation data.

18. A method according to claim 15 wherein the information relating to the internal structure is derived from Magnetic Resonance Imaging data.

19. A method according to claim 15 wherein the information relating to the internal structure is derived from Ultrasound imaging.

20. A method according to claim 15 wherein the information relating to the internal structure is derived from nuclear transmission data.

21. A method according to claim 15 wherein the initial values are based directly on image intensity values.

22. A method according to claim 21 wherein the initial values are based on different tissue densities within body tissue.

23. A method for producing a nuclear medicine image of body tissue utilizing emission data comprising:

providing information relating to the internal structure of a patient;

providing nuclear emission data acquired from the patient;

determining initial values for an iterative three dimensional reconstruction process of the emission data, based on the internal structure information; and reconstructing an image from the emission data staffing from the initial values, utilizing an iterative reconstruction process in which the emission data is isotropic, wherein the initial values comprises more than two values.

* * * * *

UNITED STATES PATENT AND TRADEMARK OFFICE
CERTIFICATE OF CORRECTION

| | | |
|---|---|---|
| PATENT NO. | : 7,197,171 B2 | Page 1 of 1 |
| APPLICATION NO. | : 10/369146 | |
| DATED | : March 27, 2007 | |
| INVENTOR(S) | : Isabella Yuzefovich et al. | |

It is certified that error appears in the above-identified patent and that said Letters Patent is hereby corrected as shown below:

In the Claims:

Claim 23 at Column 6, Line 47 change "staffing" to --starting--.

Signed and Sealed this

Twenty-fifth Day of September, 2007

JON W. DUDAS
*Director of the United States Patent and Trademark Office*